US009194803B2

(12) United States Patent
Maquelin et al.

(10) Patent No.: US 9,194,803 B2
(45) Date of Patent: Nov. 24, 2015

(54) METHOD FOR TYPING AND IDENTIFICATION OF MICRO-ORGANISMS

(75) Inventors: Kornelis Maquelin, Den Haag (NL); Maarten Jan Scholtes, Giessenburg (NL); Hendrina Francisca Maria Willemse-Erix, Raamsdonkveer (NL); Tom Christian Bakker Schut, Zoetermeer (NL); Gerwin Jan Puppels, Rotterdam (NL)

(73) Assignee: RIVER DIAGNOSTICS B.V., Rotterdam (NL)

( * ) Notice: Subject to any disclaimer, the term of this patent is extended or adjusted under 35 U.S.C. 154(b) by 782 days.

(21) Appl. No.: 12/669,366

(22) PCT Filed: Jul. 17, 2008

(86) PCT No.: PCT/NL2008/050492
§ 371 (c)(1),
(2), (4) Date: Mar. 4, 2011

(87) PCT Pub. No.: WO2009/011585
PCT Pub. Date: Jan. 22, 2009

(65) Prior Publication Data
US 2011/0143391 A1 Jun. 16, 2011

(30) Foreign Application Priority Data
Jul. 17, 2007 (NL) ................. PCT/NL2007/050355

(51) Int. Cl.
*C12Q 1/04* (2006.01)
*G01N 21/65* (2006.01)

(52) U.S. Cl.
CPC .......... *G01N 21/65* (2013.01); *G01N 2021/656* (2013.01)

(58) Field of Classification Search
None
See application file for complete search history.

(56) References Cited

U.S. PATENT DOCUMENTS

2005/0185178 A1    8/2005   Gardner

OTHER PUBLICATIONS

Rosch et al., Chemotaxonomic Identification of Single Bacteria by Micro-Raman Spectroscopy: Application to Clean-RoomRelevant Biological Contaminations, 2005, Appl. Environ. Microbiol. 71(3): 1626-1637.*
Martens et al., Extended multiplicative signal correction and spectral interference subtraction: New preprocessing methods for near infrared spectroscopy, 1991, Journal of Pharmaceutical and Biomedical Analysis 9(8): 625-635.*
De Gelder et al., Methods for extracting biochemical information from bacterial Raman spectra: An explorative study on *Cupriavidus metallidurans*, 2007, Analytica Chimica Acta 585(2): 234-240.*
Maquelin et al., Identification of medically relevant microorganisms by vibrational spectroscopy, 2002, Journal of Microbiological Methods 51(3): 255-271.*
Ivleva et al., Characterization and discrimination of pollen by Raman microscopy, 2005, Analytical and Bioanalytical Chemistry 381(1): 261-267.*
Sobin et al., The Isolation and Absorption Spectrum Maxima of Bacterial Carotenoid Pigments, 1942, J. Bacteriol. 44(3):265.*
Rhoades et al., Investigation of the Impact of Latex Components on the Survival of *Pseudomonas aeruginosa*, 2005, JCT Research 2(8): 607-615.*
Wood BR et al: "A portable Raman acoustic levitation spectroscopic system for the identification and monitoring of algal cells", Analytical Chemistry, American Chemical Society, Columbus, US, vol. 77, No. 5, Aug. 1, 2005, pp. 4955-4961.
Greene et al: "Total internal reflection Raman spectroscopy of barley leaf epicuticular waxes in vivo", Colloids and surfaces, B. Biointerfaces, Elsevier, Amsterdam, NL, vol. 45, No. 3-4, Nov. 10, 2005, pp. 174-180.
Andreeva A et al: "Light induced changes in Raman scattering of carotenoid molecules in Photosystem i particles", Proceedings of SPIE—The International Society for Optical Engineering—14th International School on Quantum Electronics: Laser Physics and Applications 2007 SPIE US, vol. 6604, Sep. 18, 2006, figures 3,4.
Andreeva Atanaska et al: "Selective photobleaching of chlorophylls and carotenoids in photosystem I particles under high-light treatment." Photochemistry and Photobiology, vol. 83, No. 6, May 23, 2007, pp. 1301-1307.
Choo-Smith L-P et al: "Investigating microbial (micro) colony heterogeneity by vibrational spectroscopy", Applied and Environmental Microbiology, American Society for Microbiology, American Society for Microbiology, US, vol. 67, No. 4, Apr. 1, 2001, pp. 1461-1469.
Schut Tom C Bakker et al: "Intracellular carotenoid levels measured by Raman microspectroscopy; Comparison of lymphocytes from lung cancer patients and healthy individuals." International Journal of Cancer, vol. 74, No. 1, 1997, pp. 20-25.
Puppels et al. Laser Irradiation and Ramanspectroscopy of Single Living Cells and Chromosomes—Sample Degradation Occurs With 514.5nm But Not With 660nm Laser-Light. Experimental Cell Research vol. 195 pp. 361-367 (1991).

* cited by examiner

*Primary Examiner* — Robert Yamasaki
(74) *Attorney, Agent, or Firm* — Reed Smith LLP; Maryellen Feehery Hank

(57) ABSTRACT

The invention relates to a method for typing or identification of a micro-organism using vibrational spectroscopy, characterised in that, differences in one or more vibrational spectroscopic signal contributions from one or more bleachable components between different spectra obtained of a sample of said micro-organism, and/or between spectra of different samples of said micro-organism, and/or between spectra of samples of different micro-organisms, are substantially eliminated as a source of signal variance in a dataset of said spectra, said bleachable components being molecules possessing vibrational spectral bands that upon exposure to light show a reduction in signal intensity.

17 Claims, 9 Drawing Sheets

METHOD FOR TYPING AND IDENTIFICATION OF MICRO-ORGANISMS

RELATED APPLICATIONS

This application is the United States national stage of International Application No. PCT/NL2008/050492, filed Jul. 17, 2008, which was published under PCT Article 21 in English as International Publication No. WO 2009/011585 A1 and which claims benefit of International Application No. PCT/NL2007/050355 filed Jul. 17, 2007.

FIELD OF THE INVENTION

The invention relates to methods for typing and identification of micro-organisms, in particular to such methods using vibrational spectroscopy for identification of micro-organisms at high resolution, i.e. at subspecies level.

BACKGROUND OF THE INVENTION

Vibrational (e.g. Raman) spectroscopy has been used to identify micro-organisms at various taxonomic levels including species level, subspecies level and strain level. Subspecies level typing of micro-organisms enables epidemiological studies. For example, it can be used to determine that different patients in a hospital have been infected with the same micro-organism, which may point at a common source of infection (e.g. a contaminated instrument). This will then enable targeted hygienic measures to be taken. It could also point out that a microbial strain has been transmitted between patients and that measures such as isolation of infected patients may be required. It is estimated that in the industrialized world about 5 to 10% of the patients admitted to a hospital will develop a microbial infection during their stay. These nosocomial or hospital acquired infections are the cause of much patient suffering and place a high financial burden on the health care system. It has been shown that programs based on routine subspecies typing of patient material, by means of which contaminations or outbreaks of infections can be recognized at an early stage, can be very cost-effective. However, such programs are not in place in most hospitals and routine identification of micro-organisms is essentially limited to the species level, which does not provide the epidemiological information to enable early detection of outbreaks and contaminations.

Current methods for microbial typing, both genotyping and phenotyping methods, are not suitable for routine application in hospitals. They are generally costly, have a sample throughput that is too low to keep up with the flow of patient samples in a hospital, and require expert operators and special facilities.

Vibrational spectroscopy does not have these drawbacks and is a good candidate for routine microbial typing. However identification at strain level puts high demands on the reproducibility of the Raman measurements, due to the fact that the spectral differences between closely related strains can be very small. For example, it has been found that there can be greater than 99.9% correlation between Raman spectra of closely related strains. This implies that technology protocols for sample preparation and measurement, and data analysis algorithms used to obtain and analyze Raman spectra of microbial strains must result in a reproducibility of better than 99.9%.

Escoriza et al. (*Appl. Spectrosc.* 2006, 60(9), 971-976) describe the monitoring of growth curves of *Escherichia coli* and *Staphylococcus epidermidis* by Raman spectroscopy over extended periods of time (days) with the aim of identifying spectral variations throughout the growth cycle. In order to increase the signal to noise ratio, the fluorescence background signal, which is well-known to be present in biological samples, is bleached by prolonged laser irradiation, without affecting the Raman signal. In this document the Raman spectra of two strains belonging to different species and Gram-types are compared.

The technique of reducing the signal to noise ratio by bleaching the fluorescence background signal is also described by Esposito et al. (*Appl. Spectrosc.* 2003, 57(7), 868-871). Residual fluorescence can be removed by a polynomial fit. This is a mathematical procedure in which low frequency background signal, modelled by means of a polynomial function, fitted to the spectrum, is substracted from the Raman spectrum with fluorescent background. There is no guarantee that the shape of the polynomial resembles the actual shape of the fluorescence background. Although this document provides a number of spectra for individual spores that look very similar, it is noted that this document mentions that approximately 4% of the spores studied exhibited no Raman scattering attributable to calcium dipicolinate, and therefore yielded remarkably different Raman spectra. There is no suggestion in this document how to deal with this signal variance.

US-A-2005/0 185 178 describes the use of wide field Raman spectroscopy to quickly identify biological agents and pathogens. Photobleaching of substantial areas of the sample reduces the overall fluorescent background signal to enhance the Raman signal to noise ratio.

The vibrational spectroscopy-based microbial typing techniques described in the prior art, such as for instance disclosed in EP-A-1 623 212, comprise standardization of sample preparation. An important step is culturing of the patient material for a defined period of time on a standardized culture medium. After inoculation the micro-organisms in the patient sample will start to grow and divide and after a number of cell division cycles the cells will be in a growth condition that is independent of the condition of the micro-organism in the patient sample at the start of the culturing step. In this way, variance in the molecular composition of cells belonging to the same strain, but obtained from different sources, can be minimized.

However, standardization of culture conditions has been found to not always be sufficient to reduce intra-strain variance in molecular composition to the point where it no longer interferes with subspecies identification of micro-organisms by means of Raman spectroscopy. Differentiation of strains of microbial species based on their Raman spectra is then hindered because of the presence of molecular constituents of which the Raman signal contribution to the spectrum varies relatively strongly from one sample of a strain to the next sample of the same strain, despite the fact that the sample preparation procedure including the sample culturing have been standardized.

This is for instance the case for *Staphylococcus aureus*, *Pseudomonas aeruginosa* and *Mycobacterium* strains. The Raman spectra of some of these strains show significant intra-strain qualitative variance in signal intensity, i.e. variations in relative signal intensity and shape of the bands of the spectra, e.g. throughout the 400 to 1800 $cm^{-1}$ spectral region, hereafter referred to as the fingerprint region, between repeat cultures of the same strain.

Some of these signal variations are due to signal contributions of carotenoids, which can be present in abundance in *S. aureus*. Carotenoids generally show strong signal contributions at about 1004 $cm^{-1}$, 1525 $cm^{-1}$ and at 1157 $cm^{-1}$. At these locations in the Raman spectrum, there is little overlap with signal contributions due to other molecular constituents, Therefore, if variance in signal intensity of these Raman bands affects the signal analysis, this can simply be remedied by eliminating these spectral regions from the analysis. However, it was found that spectra of *S. aureus* show significant signal variations essentially in all parts of the fingerprint region, from 400-1800 $cm^{-1}$. This signifies the presence of other as yet unidentified constituents in *S. aureus* cells of which the concentration can vary significantly between repeated sample preparations. The resulting large variance in signal intensity of these molecular constituents negatively affects the reproducibility with which Raman spectra of *S. aureus* strains can be measured and thereby negatively affects the possibility to identify *S. aureus* isolates at the strain level.

With respect to hospital-acquired infections, methicillin resistant *S. aureus* (MRSA) strains are one of the largest problems in hospitals, worldwide. Any broadly applicable method for routine microbial typing must therefore be able to also type *S. aureus* strains.

Therefore, in order for vibrational spectroscopy to be applicable for routine strain-level identification of patient isolates, this problem must be resolved. Similar problems have been encountered in other species, e.g. *Mycobacterium* species. Therefore there exists an ongoing need for improving microbial typing techniques using vibrational spectroscopy.

SUMMARY OF THE INVENTION

The present inventors have now found a method for typing or identification of a micro-organism which does not suffer from the problems of the prior art methods.

The present invention provides in a first aspect a method for typing or identification of a micro-organism using vibrational spectroscopy, characterised in that, differences in one or more vibrational spectroscopic signal contributions from one or more bleachable components between different spectra obtained of a sample of said micro-organism, and/or between spectra of different samples of said micro-organism, and/or between spectra of samples of different micro-organisms, are substantially eliminated as a source of signal variance in a dataset of said spectra, said bleachable components being molecules possessing vibrational spectral bands that upon exposure to light show a reduction in signal intensity.

An advantage of the method is that signal variance in a database of spectra of micro-organisms due to variance in signal contribution of these bleachable components is essentially eliminated or reduced to such an extent that strain-level identification is possible.

The sample of at least one micro-organism is typically a sample of a culture of said micro-organism, preferably a sample of a pure culture.

In a preferred embodiment, identification of said one or more vibrational spectroscopic signal contributions of said one or more bleachable components in one or more samples of one or more micro-organisms comprises providing at least two vibrational spectra from said one or more samples recorded at different time points, wherein at least one of said at least two vibrational spectra is recorded during or after photobleaching of said sample. Preferably, said at least two spectra are subtracted from each other to provide a difference-spectrum, which enables the identification of said one or more vibrational spectroscopic signal contributions in spectra of said one or more samples of said one or more micro-organisms.

The sample of micro-organisms is preferably subjected to photobleaching to such extent that the intensity of the spectral bands of bleachable components is reduced when compared to conditions wherein said sample is not subjected to photobleaching.

The photobleaching is preferably performed under laser light. Photobleaching is generally carried out for at least 1 second. Bleachable components are best identified and eliminated from the vibrational spectra when samples are subjected to photobleaching for longer periods of time. Suitable times are for instance 10-1 000 seconds, preferably around 100-600 seconds. Good results are obtained with 200 seconds of photobleaching, e.g. when a laser light of 785 nm and with a power of 100 mW or more is focused on a microbial sample, depending on microbial species.

It is preferred that photobleaching is performed using the same laser light source as is used for obtaining vibrational spectroscopic information about the one or more samples.

Multiple spectra are suitably recorded over a period time from one or more samples of one or more micro-organisms while said one or more samples are being subjected to photobleaching, and wherein the one or more vibrational spectroscopic signal contributions of the one or more bleachable components are identified from the multiple spectra thus obtained. This may for instance be performed by averaging series of consecutively recorded spectra, and comparing these to averaged series of consecutively recorded spectra recorded after (prolonged) photobleaching.

In methods of the present invention it is preferred to record spectra from different (spatially separated) locations of said sample, in order to compensate for spatial variation in molecular composition within the sample itself.

In a preferred embodiment, said identified one or more vibrational spectroscopic signal contributions of said one or more bleachable components are used to substantially eliminate said differences in said vibrational spectroscopic signal contributions from said one or more bleachable components as a source of vibrational spectroscopic signal variance in a dataset of micro-organism spectra.

The substantial elimination of said vibrational spectroscopic signal variance in said dataset of micro-organism spectra can be accomplished by using said identified one or more vibrational signal contributions of said one or more bleachable components in an approach based on Extended Multiple Scatter Correction—Spectral Interference Substraction (see Martens and Stark, J. Pharm. Biomed. Anal. 1991, Vol. 9(8): 625-35).

The spectra can be intensity normalized by dividing the spectra by the intensity integral in the spectral interval from 1432 $cm^{-1}$ to 1498 $cm^{-1}$ in which primarily signal contributions from $CH_2$ and $CH_3$ bending and deformation modes are found.

For the purpose of typing or identification of micro-organisms based on their corrected vibrational spectroscopic information, a reference dataset can be provided comprising corrected vibrational spectroscopic information of at least one micro-organism. Said reference dataset can consists of spectra obtained from substantially photo-bleached micro-organism samples, from substantially non-photo-bleached micro-organism samples, or from substantially non-photo-bleached micro-organism samples and photo-bleached micro-organism samples.

The dataset thus obtained may be ordered by hierarchically clustering the corrected vibrational spectroscopic information in said data set. Hierarchical clustering is suitably performed on Principal Component scores obtained by principal component analysis of the corrected vibrational spectroscopic information. The hierarchical clustering has the advantage that an ordering in said dataset is established which may serve as a reference for typing and identification purposes against which additional (untyped or unidentified) micro-organisms may be compared.

Thus a micro-organism may be typed or identified by a method of the present invention by obtaining corrected vibrational spectroscopic information by a method as described above for a micro-organism of interest and comparing the corrected vibrational spectroscopic information thus obtained to a reference dataset obtained in an embodiment of the invention wherein multiple organisms have been subjected to the same method.

The method of the present invention is suitable for any micro-organism, and has found important utility in typing and identification of strains of *Staphylococcus aureus, Pseudomonas aeruginosa*, and *Mycobacterium*.

DETAILED DESCRIPTION OF THE INVENTION

Definitions

Figure 1:
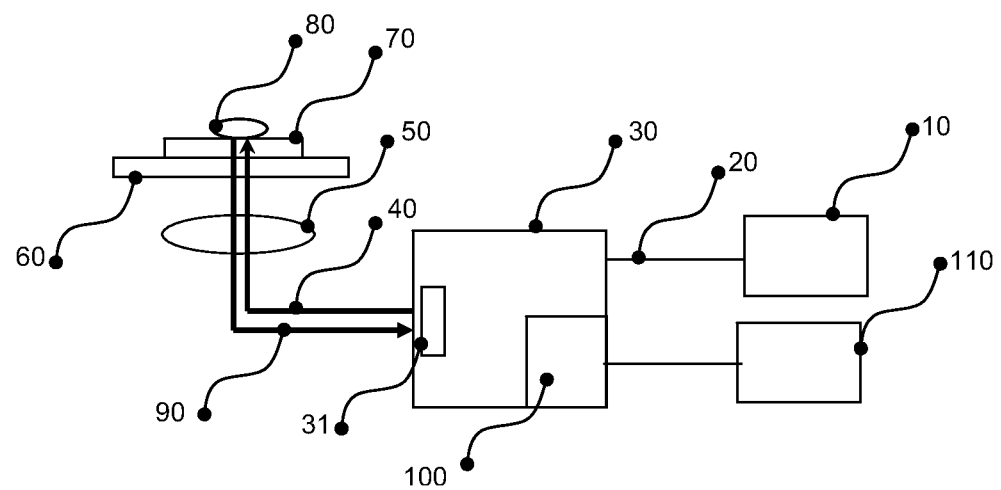
FIG. 1 schematically shows a measurement setup.

The term "typing" as used herein is defined as the discrimination of individual strains within a given species. It has significance in a number of areas including microbial taxonomy, phylogenetic relationships, epidemiological investigation of outbreaks of infectious diseases and determination of genetic diversity in relation to relevant biological properties such as pathogenicity and drug resistance. The term broadly encompasses typing of expressed characteristics (i.e. phenotyping such as serotyping, biochemical profiling, chemical susceptibility profiling, and spectroscopic typing) as well as molecular typing methods (genotyping).

The term "identification" as used herein is defined as the process of determining the taxonomic position of a micro-organism in a pre-determined classification system. Such a classification system is very suitably a data set consisting of corrected vibrational spectroscopic information from multiple micro-organisms that is hierarchically clustered.

The term "micro-organism" as used herein is defined as microscopic organism, including bacteria (e.g. gram positive and gram negative cocci and gram positive and gram negative bacilli, mycoplasmas, rickettsias, actinomycetes, and archaeobacteria), fungi (fungi, yeast, molds), and protozoa (amoebae, flagellates, ciliates, and sporozoa). While viruses (naked viruses and enveloped viruses) and prions are not minute "living" organisms as typically ascribed to the term micro-organism, for purposes of this disclosure they are included in the term micro-organism because of their effect on biological systems. The term micro-organism also encompasses quiescent forms of microscopic organisms such as spores (endospores). In particular, micro-organisms include bacteria, more preferably pathogenic bacteria for which typing at subspecies level is required, such as bacteria of the following genera and species, which listing is not intended to be limiting: *Acinetobacter* (e.g. *A. Iwoffii* and *A. baumannii*), *Actinomyces* (e.g. *A. israelii*), *Aerococcus* (e.g. *A. viridans*), *Aeromonas* (e.g. *A. hydrophile* and *A. salmonicida*), *Alcaligenes* (e.g. *A. faecalis*), *Alicyclobacillus* (e.g. *A. acidocaldarius*), *Anaplasma* (e.g. *A. marginals* and *A. ovis*), *Bacillus* (e.g. *B. anthracis* and *B. cereus*), *Bacteroides* (e.g. *B. fragilis*), *Bartonella* (e.g. *B. bacilliformis, B. henselae* and *B. quintana*), *Bordetella* (e.g. *B. pertussis*), *Borrelia* (e.g. *B. burgdorferi* and *B. recurrentis*), *Brevibacterium* (e.g. *B. linens*), *Brucella* (e.g. *B. melitensis* biovar *abortus* and *B. m.* biovar *canis*), *Burkholderia* (e.g. *B. cepacia*), *Campylobacter* (e.g. *C. jejuni*), *Capnocytophaga* (e.g. *C. canimorsus*), *Chlamydia* (e.g. *C. trachomatis, C. pneumoniae* and *C. psittaci*), *Chromobacterium* (e.g. *C. violaceum*), *Citrobacter* (e.g. *C. freundii*), *Clostridium* (e.g. *C. botulinum, C. difficile, C. perfringens* and *C. tetani*), *Corynebacterium* (e.g. *C. diphtheriae*), *Cowdria* (e.g. *C. ruminantium*), *Coxiella* (e.g. *C. burnetii*), *Edwardsiella* (e.g. *E. tarda*), *Ehrlichia* (e.g. *E canis, E. chaffeensis* and *E. phagocytophila*), *Eikenella* (e.g. *E. corrodens*), *Enterococcus* (e.g. *E. faecium* and *E. faecalis*), *Escherichiae* (e.g. *E. coli*), *Flavobacterium* (e.g. *F. meningosepticum*), *Fluoribacter* (e.g. *F. dumoffii*), *Francisella* (e.g. *F. tularensis*), *Fusobacterium necrophorum, Gardnerella* (e.g. *G. vaginalis*), *Gemella* (e.g. *G. morbillorum*), *Haemophilus* (e.g. *H. influenzae* and *H. ducreyi*) *Helicobacter* (e.g. *H. pylori, H. cinaedi* and *H. fennelliae*), *Kingella* (e.g. *K. denitrificans*), *Klebsiellae* (e.g. *K. pneumoniae*), *Legionella* (e.g. *L. pneumophila* and *L. micdadei*), *Leptospira* (e.g. *L. interrogans*), *Leuconostoc* (e.g. *L. pseudomesenteroides*), *Listeria* (e.g. *L. monocytogenes*), *Micrococcus* (e.g. *M. luteus*), *Moraxella* (e.g. *M. catarrhalis*), *Morganella morganii, Mycobacterium* (e.g. *M. tuberculosis, M. lepra, M. africanum, M. bovis* and *M. avium*), *Mycoplasma* (e.g. *M. pneumoniae*), *Neisseria* (e.g. *N. meningitidis* and *N. gonorrhoeae*), *Neorickettsia* (e.g. *N. helminthoeca*), *Nocardia* (e.g. *N. asteroides*), *Pasteurella* (e.g. *P. multocida*), *Pedio-*

*coccus* (e.g. *P. acidilactici*), *Peptostreptococcus* (e.g. *P. prevotii*), *Plesiomonas* (e.g. *P. shigelloides*), *Prevotella* (e.g. *P. intermedia*), *Propionibacterium propionicum*, *Proteus* (e.g. *P. mirabilis*), *Providencia* (e.g. *P. alcalifaciens*), *Pseudomonas* (e.g. *P. aeruginosa* and *P. cepacia*), *Rickettsia* (e.g. *R. prowazekii* and *R. typhi*), *Rickettsiella* (e.g. *R. popilliae*), *Salmonellae* (e.g. *S. typhimurium* and *S. enteritidis*), *Serratia* (e.g. *S. marcescens*), *Shigella* (e.g. *S. dysenteriae*), *Staphylococcus* (e.g. *S. aureus* and *S. pyogenes*), *Stenotrophomonas* (e.g. *S. maltophila*), *Streptobacillus moniliformis*, *Streptococcus* (e.g. *S. pneumoniae*, α-, β- and γ-haemolytic and viridans and *S. pyogenes*), *Tatlockia* (e.g. *T. micdadei*), *Treponema* (e.g. *T. pallidum*), *Veillonella* (e.g. *V. parvula*), *Vibrio* (e.g. *V. cholerae*, *V. vulnificus* and *V. parahaemolyticus*), *Wolbachia* (e.g. *W. pipientis*), *Yersinia* (e.g. *Y. enterocolitica* and *Y. pestis*).

The term "Raman spectroscopy" as used herein is defined as a spectroscopic technique used in condensed matter physics and chemistry to study vibrational, rotational, and other low-frequency modes in a system. It relies on inelastic scattering, or Raman scattering of monochromatic light, usually from a laser in the visible, near infrared, or (near) ultraviolet range. Molecular vibrational motions, rotational motions, or phonons in said system which are illuminated with said laser light, are excited or de-excited as a result of a Raman scattering event, resulting effectively in an exchange of energy between molecules and the incident electromagnetic field. As a result, the scattered light contains wavelengths other than that of the incident light, which provides information about the molecular energy levels and phonon energy levels in the system under investigation. Typically, a sample is illuminated with a laser beam. Light which is scattered by the sample from the illuminated spot is collected with a lens and sent through a monochromator. Wavelengths close to the laser line (due to elastic Rayleigh scattering) are filtered out and those in a certain spectral window away from the laser line are dispersed onto a detector. A Raman spectrum is a set of very narrow spectral lines emitted from object molecules when illuminated by an incident light. The width of each spectral line is strongly affected by the spectral width of the incident light and hence tightly monochromatic light sources, such as lasers, are used. The wavelength of each Raman line is expressed as a wavenumber-shift from the incident light, which is the difference between the inverse wavelength of the Raman line and the incident light. The wavenumber-shift, not the absolute wavenumber, of the Raman lines is specific to particular atomic groups in molecules. Raman spectra measure the vibrational modes of molecules which are determined by their composition and molecular structure, and molecular sub-groups, e.g. by atomic groups within molecules such as methylene, ethylene, amide, phosphate or disulphide. Most applications of Raman spectroscopy in biology are concerned with changes in vibrational modes of macromolecules or small molecules. For example, changes in either the wavenumber-shift of single Raman lines or the relative intensities of two or more Raman lines in an atomic group within a molecule have been interpreted as indicating conformational changes in macromolecules. For these reasons Raman spectroscopy has been used for qualitative studies of molecules and molecular dynamics in biology. For easier and clearer interpretation of Raman spectra, use of the technique has been restricted mainly to purified materials and their systems, such as enzyme reactions. However, because Raman spectra are based on the highly specific vibrations of molecules or atomic groups within molecules, they can also be used to characterize and quantify a mixture of molecules as compositions of atomic groups within molecules by a method akin to fingerprinting. Although unable to resolve the composition of a complex biological samples, such as cells or tissues, in terms of a list of chemical compounds in great detail, the Raman spectrum of the sample does in a way represent and provide a rough sketch of the molecular composition of that sample and of how it may change with time.

The term "corrected vibrational spectroscopic information" refers to any information obtained from vibrational spectroscopic analysis of micro-organisms, in particular Raman spectra, from which spectral information derived from bleachable components is eliminated. When hierarchically clustered, the spectral information can provide sufficient information to classify and identify micro-organisms at the subspecies level.

The term "bleachable component" as used herein is defined as a particular molecule or atomic group within a molecule, i.e. a molecular moiety within a molecule or a molecule itself, that generates vibrational spectral lines, and which group or moiety or molecule has the tendency to generate spectral lines of lower intensity upon exposure to light, in particular laser light as used in Raman excitation. The lower intensity upon illumination by the Raman laser gives the impression that the component "bleaches".

The term "photobleaching" as used herein refers to a physical effect or process involving modification of the molecule or atomic group by photons, that limits the signal or intensity of emitted light collected from the object in a particular spectral line or in multiple spectral lines.

"Principal Component" (PC) analysis is a mathematical manipulation of a data matrix where the goal is to represent the variation present in many variables using a small number of 'factors'. A new row space is constructed in which to plot the samples by redefining the axes using factors rather than the original measurement variables. These new axes, referred to as factors or principal components (PCs), allow the analyst to probe matrices with many variables and to view the true multivariate nature of data in a relatively small number of dimensions. (K. S. Beebe, R. J. Pell, and M. B. Seasholtz Chemometrics: a practical guide, John Wiley & Sons: New York. 1998, pp. 81-82). The first principal component (PC1) represents the direction in the data set in which the maximum amount of variation is present: it lies in the direction of maximum spread of data points. The second principal component (PC2), defined as orthogonal to (and independent from) the first, explains the maximum variation possible using the remaining variations not explained in PC1. The third principal component, defined as orthogonal to (and independent from) the first and second, explains the maximum variation possible using the remaining variations not explained in PC1 and PC2, and so on. Each sample will have one co-ordinate (called a score) along each of the PCs. Therefore, the sample can for example be located on a 2-dimensional PC Score Plot using the two co-ordinates of the two selected PCs.

The term "signal variance" as used herein refers to the variance encountered in a collection of spectra, with respect to the number of peaks and bands in the spectral interval of interest, the wavenumber-shift of these peaks and bands, and their width, shape, polarization, and relative intensities.

The present inventors found that bacterial samples comprise components that are responsible for significant variation in vibrational spectroscopic results, in particular Raman spectroscopic results, and thereby hinder differentiation of strains of microbial species based on their Raman spectra due to the fact that the vibrational signal contribution of these components to the total vibrational spectrum varies relatively strongly from one sample of a strain to the next sample of the same strain. It is believed that inter alia carotenoids belong to this group of compounds. Carotenoids are very strong Raman scatterers, compared to most other biological molecules. They are also light sensitive. Under laser illumination the well known Raman spectral features of carotenoids slowly bleach, i.e. they decrease in intensity.

Surprisingly it was found that the vibrational signal (in particular the Raman signal) of these strongly varying constituent components is subject to bleaching, whereas the other molecular constituents of the microorganisms are less, or not.

Raman spectra were obtained of the partly unidentified bleachable molecular species by recording spectra of *S. aureus* strains before and after bleaching of these species and by calculation of a difference spectrum of the spectra before and after bleaching.

The signal variance in spectra of *S. aureus*, which is due to these bleachable constituents can then be eliminated, e.g. by means of a spectrum processing procedure referred to as extended multiple scatter correction, in which the spectrum or multiple spectra of bleachable *S. aureus* constituents are used as so-called interferent(s).

The present inventors have found that by means of this procedure the effects of biological signal variance encountered in *S. aureus* strains, which is difficult to control by means of standardization of sample preparation procedures, can essentially be reduced to a level at which it does not interfere with identification at subspecies level any longer.

The same procedure, of determining the spectral signatures of the complex of bleachable constituents and using these to eliminate the spectral variance due to these features in spectra of microbial species, was also found to improve microbial identification, when applied to other microbial species, such as *Pseudomonas aeruginosa* strains and *Mycobacterium* strains.

In a preferred embodiment, the method of the present invention comprises the elimination of the vibrational spectral lines of bleachable components from the spectra. This may occur in various ways. For instance, a sample may be subjected to photobleaching prior to analysis. In this way, the contribution to the spectrum of spectral lines from bleachable components is diminished. This is best done by producing a difference spectrum (generated by subtracting two spectra from one another, i.e. subtracting a spectrum of a photobleached sample from a spectrum of a less photobleached or non-photobleached sample) and deducing from a difference spectrum the spectral lines derived from the bleachable components. These will be presented in the difference spectrum as lines having a residual intensity. Once these spectral lines have been identified, the signal variance in datasets of spectra caused by these lines can be substantially eliminated. In this way a corrected vibrational spectrum (spectra) is obtained.

In a particularly preferred embodiment, the spectrum of bleachable components, e.g. as determined by the method described above is used to substantially eliminate the signal variance in a dataset of micro-organism spectra, which are due to the varying spectral contributions of these bleachable spectral components, e.g. by spectral interference subtraction (Martens, H. and E. Stark, *Extended multiplicative signal correction and spectral interference subtraction: new preprocessing methods for near infrared spectroscopy. J Pharm Biomed Anal* 1991, 9(8), 625-35).

Sample of Interest and Its Preparation

A vibrational spectrum of the micro-organism in the sample of interest is generally obtained after culturing the micro-organism in the sample of interest under appropriate conditions for propagation. If convenient or required, the sample of interest is then transferred to carrier material, such as an aluminum foil or fused silica window.

Depending on the vibrational technique which is used, suspensions may be standardized and inoculum density may be adjusted in order to obtain homogeneous films and reproducible results. However, in one embodiment cultures are subjected to spectrometry without sample preparation and are measured directly on their culture medium.

Typically, the micro-organisms in the sample of interest are cultured by incubating the sample of interest in or on a suitable culture medium. The culture medium may be solid, which will result in colonies of biomass. The colonies are grown at a temperature which mimics the situation at the place from which the sample of interest was taken, for many human pathogens this will typically be between 30° C. and 37° C., for a period which is long enough, typically about 4-8 hours, to obtain at least microcolonies. Microcolonies are colonies with a diameter of about 10-100 micrometer and a vibrational spectrum of microcolonies may be obtained in the instrument of the present invention while they are still on the solid culture medium. Larger colonies may be obtained by culturing for a longer period, e.g. about 16-24 hours. A vibrational spectrum from larger colonies may be obtained by streaking out part of the colony biomass on carrier material, creating a "smear". Even as little as one single cell may be used for obtaining a vibrational spectrum.

Alternatively, the culture medium may be a liquid culture medium. Micro-organisms may be harvested from such liquid culture medium by methods known in the art, e.g. by centrifugation. The concentrated micro-organisms may then be transferred to carrier material, optionally after drying, for obtaining a vibrational spectrum.

The sample of interest may be any kind of material including, but not limited to, patient material such as blood, urine, feces, intravenous catheters etc., industrial production lines, water systems, a food product, a cosmetic product, a pharmaceutical product and a forensic sample. The sample may also be a swab from an instrument, furniture, walls, doors, or e.g. a faucet. Patient material is typically taken from and not returned to the patient. It may be taken from a living patient or it may be taken post-mortem.

Spectroscopy

Any type of IR spectroscopy may be used to obtain a vibrational spectrum, such as absorption/transmission, absorption/reflection, diffuse reflection and attenuated total reflection IR spectroscopy. In one embodiment, Fourier transform IR microspectroscopy is used. For IR microspectroscopy, suspensions of small amounts of micro-organisms are typically cultivated on an appropriate nutrient agar plate, for e.g. about 16-24 hours at about 37° C. Small amounts of the micro-organism are removed from the agar plate and suspended in distilled water and a droplet of the suspension is then transferred to a carrier. Spectra may be obtained from liquid solutions, suspensions or viscous or solid films which have been cast on a suitable carrier. Suitable carriers are IR-transparent plates which are water-insoluble and include materials such as $CaF_2BaF_2$, ZNSe, ZnS and germanium. If a spectrum is obtained from a film, the droplet may be dehydrated in a desiccator over a drying agent, such as silica gel, under a moderate vacuum, to form a transparent film. The optical plate containing the microbial preparation is then sealed in a gas-tight cuvette cartridge and placed in the spectrometer. When spectra are obtained from microcolonies, diluted biomass suspensions are typically incubated for about 6-10 hours at about 37° C., before they are transferred from the agar nutrient plate to a suitable IR-transparent window. For IR spectroscopy on both colonies and microcolonies, suspensions are typically standardized and inoculum density is adjusted in order to obtain homogeneous films and reproducible results, although this may not always be strictly necessary.

Preferably, the instrumental parameters are kept constant for all measurements which have to be compared. A suitable set of parameters would be a nominal spectral resolution of between 1 and 15 cm$^{-1}$ and a sufficient number of scans to obtain a signal-to-noise ratio of between 1 000:1 and 10 000:1. In one embodiment, the nominal physical resolution is 6 cm$^{-1}$ and the signal-to-noise ratio is better than 3 000:1.

The term vibrational spectroscopy encompasses both IR spectroscopy and Raman spectroscopy. Infrared spectroscopy yields similar, but complementary information to Raman spectroscopy. In preferred embodiments, Raman spectroscopy is used in methods of the present invention.

Any type of Raman spectroscopy may be used to obtain a vibrational spectrum, such as ultraviolet (UV) resonance Raman spectroscopy, Fourier transform (FT) Raman spectroscopy and visible or near infrared (NIR) multichannel Raman spectroscopy. In one embodiment, confocal Raman microspectroscopy is used. In general, Raman samples need less preparation than IR samples. There is e.g. no need inoculum density adjustment. Typically, some biomass from microcolonies (6-10 hours at 37° C.) or from colonies (15-20 hours at 37° C.) is smeared on an optical substrate, such as CaF$_2$ or fused silica, and placed positioned in the laser beam of a Raman spectroscopy instrument, preferably a multichannel NIR-Raman microspectrometer. Alternatively, the samples may be air dried or dried in a desiccator and then be placed in the laser beam of a Raman spectroscopy instrument. In a preferred embodiment, the samples are measured directly on the surface of the culture plate.

The sample is typically illuminated by a monochromatic light source with a line width sufficiently narrow to enable measurement of the desired Raman signal of a sample with sufficient spectral resolution, such as a laser. Lasers preferably have an excitation power of greater than 50 mW to limit the signal collection time. For high laser powers the sample may be scanned through the laser focus during measurements or the laser beam may be scanned over the sample in order to distribute the laser power over a larger sample surface and thus prevent sample degradation. In one embodiment, a diode laser emitting laser light of 785 nm and delivering 100 mW of laser power to the sample is used.

A suitable excitation wavelength is at least 630 nm to avoid laser light induced damage to the sample and to minimize fluorescence scattering in the sample. In one embodiment, an excitation wavelength of 830 nm is used.

Although any Raman spectrometer may be used, a preferred option is a dispersive multi-channel spectrometer, such as a Model 2500 High Performance Raman Module from River Diagnostics, Rotterdam, The Netherlands.

Preferably, the detector is a multi-channel detector, such as a charge coupled device (CCD) camera optimized with a light detection efficiency that is optimized for the near infrared region of the electromagnetic spectrum, in particular for the 700 to 1 000 nm wavelength region, and more particular optimized for the 785 to 950 nm wavelength region, when laser light of 785 nm is used to illuminate the samples of interest in the Raman spectroscopic measurements.

The skilled person will understand that if other laser excitation wavelengths, e.g. in the deep UV, the visible region of the electromagnetic spectrum or further out in the near-infrared region of the electromagnetic spectrum, are used, also other detectors may be used, e.g. a multichannel detector may be employed with sensitivity in the near-infrared region beyond the region where a CCD-camera can be employed, e.g. a cooled and/or image-intensified InGaAs (indium gallium arsenide) multichannel detector. Alternatively, it may in some cases be beneficial to employ a Fourier-transform Raman spectrometer to analyze a Raman signal emitted in the near-infrared, instead of a dispersive Raman spectrometer.

The detector elements of the multi-channel detector may be calibrated for the wavenumber shift of the Raman signal incident on the detector elements. In one embodiment, this calibration is repeatable and reproducible to within 0.1 wavenumbers.

Typically several spectra from different positions in the sample are taken to cover all biochemical variation present. A suitable spectral range is that which covers wavenumber shifts from 250 cm$^{-1}$ to 2 150 cm$^{-1}$. The skilled person will understand that a part or parts of this spectral range or other spectral regions outside of the 250-2 150 cm$^{-1}$ spectral region may be employed too.

The relation between the wavenumber shift cm$^{-1}$ and the wavelength shift of a Raman signal with respect to the wavelength of the monochromatic light that is incident on the sample is given by:

$$\Delta cm^{-1} = \frac{100}{\text{laser wavelength } (m)} - \frac{100}{\text{signal wavelength } (m)}$$

The skilled person will understand that corrections have to be made for signal contributions form non-sample derived signal, including but not limited to signal from the optical substrate and/or the culture medium. The spectral resolution is typically better than 5 cm$^{-1}$ preferably better than 8 cm$^{-1}$ or wavenumbers.

Preferably the quality of the spectral signal is such that signal variance as a result of noise contributions is smaller than signal variance resulting from differences in molecular composition of microbial strains to be distinguished. For example, a signal-to-noise ratio defined as the integrated signal intensity over the spectral region of 400 to 1 800 wavenumbers, after subtraction of a straight baseline between these points, divided by the square root of this signal intensity, of 3 200 was found to be sufficient to distinguish microbial strains isolated in 5 different outbreaks of infections by Acinetobacter strains.

It will be clear to the skilled person that this number may be species-dependent and that it may therefore be advisable to measure spectra as a matter of standard with a signal-to-noise ratio that is higher than 3 200. Other methods of estimating the required signal-to-noise ratio may be applied.

The use of a vibrational spectroscopic technique for microorganisms is well-described in the art, e.g. in K. Maquelin et al. p. 3308 In: Handbook of vibrational spectroscopy (2002) Eds. Chalmers & Griffiths.

After the spectra have been obtained, spectra are typically pre-processed, which comprises wavenumber calibration of the detection channels, and correction for the wavelength dependent signal detection efficiency of the instrument to obtain an instrument independent wavelength dependent signal detection efficiency. Suitable methods are known in the art, such as from R. Wolthuis et al., 1999, p. 431. In W. T. Mason(ed.), Fluorescent and luminescent probes for biological activity, 2nd ed. Academic press, London.

In one embodiment using Raman microspectroscopy, this is effected by subtracting from all spectra the constant background signal contribution originating from optical elements in the laser light delivery pathway.

For calibration of the wavenumber axis of the Raman spectra of microbial samples, the emission spectrum of a Ne—Ar emission light source, of which the positions of the spectral emission lines are precisely known, can be measured. In addition, the Raman spectrum of a Raman calibration sample of inert material with precisely known Raman peaks can be measured. Emission lines of the Ne—Ar light source can then be used to convert pixel positions of a CCD camera to absolute wavenumbers. The exact position of the laser emission line in absolute wavenumbers can be determined using the spectrum of the Raman calibration sample. It is then possible to convert CCD camera pixel positions to relative wavenumbers by subtracting the laser line position (in absolute wavenumbers), from the pixel position (in absolute wavenumbers).

The wavelength dependent signal detection efficiency of the Raman measurement setup can be corrected by measuring the emission spectrum from a standard reference material and dividing the recorded spectrum by a calculated spectrum based on the emission spectrum of the standard reference material, which would be recorded if the signal detection efficiency of the Raman instrument would be wavelength independent.

Background signal, generated in the optical components of the Raman measurement setup, can be recorded separately, and subtracted from the Raman spectra obtained from microbial samples.

Subsequently, the pre-processed spectra may be entered into the analysis computer.

The computer program in operation executes computer executable software code for analysis of the signal obtained from the spectrometer and for classification of the microorganism. The analysis may be based on well known methods for developing algorithms which will enable a rapid search of the database to determine which spectrum or spectra in the database show the highest similarity with a new spectrum measured of an unknown microbial strain. Such algorithms may be developed by first applying, for example, principal component analysis, followed by linear discriminant analysis or hierarchical cluster analysis to the spectra in the database. This will organize the spectra in the database into clusters based on a measure of similarity between spectra.

Such a measure may for instance be the squared Euclidean distance between spectra.

Spectra within one cluster are generally more similar to each other than to any other spectrum in the database. Using a very powerful computer it would be feasible to perform a new cluster analysis with all spectra in the database and the newly measured spectrum of a microbial strains or spectra of a number of microbial strains, after which it is known which spectra of known microbial strains from the database are most similar to the new spectra.

Alternatively, first a classification model is developed based on a cluster analysis of the existing database of spectra of microbial strains. For example, a classification model is built by training an artificial neural network for separate branching points in the dendrogram that results from the clustering analysis. Of course other classification methods, such as but not limited to, linear discriminant analysis may be used instead of or in combination with artificial neural networks.

In one embodiment the classification model is spectroscopy guided. This means that the spectroscopic similarity between spectra itself is the input for development of the classification model.

This approach has an important advantage over approaches in which for instance the identity at genus, species and/or strain-level is the guiding principle for development of the classification model, because it does not suppose that a correlation exists between taxonomic relatedness and spectral similarity.

Another advantage of the spectroscopy guided classification model is that it enables inclusion in the model of strains that have not yet been identified or characterized, other than by vibrational spectroscopy. Using spectroscopy guided classification, only a selected part of the spectrum will suffice in constructing the classification model.

Different parts of the spectrum may be used at different steps.

All classification models may conveniently be combined with hierarchical cluster analysis. For example, the classification model may be used to limit the number of spectra to the spectra that are most similar to the new spectrum or spectra, after which as a final step a cluster analysis of this limited number of spectra from the database and the new spectrum may be performed to determine which spectrum or spectra in the database is most similar to the new spectrum. Based on spectral similarity found for the new strain and on known spectral similarities between spectra of microbial strains known to be different than the strain in the database that shows closest spectral similarity to the new strain, it may be decided that the new strain is the same as the strain already in the database and showing closest spectral similarity, or it may be decided that the new strain was not yet represented. An additional criterion may be to calculate if addition of the new spectrum to an existing cluster of spectra of a certain strain significantly increases the spectral variance within that cluster. If that is the case it may still be decided that the new spectrum belongs to a strain not yet represented in the database.

Other criteria may also be applied such as e.g. the inconsistency coefficient, which is a standard function in the statistics toolbox of MATLAB-programming software (The Mathworks inc, Natick, Mass., USA).

More computational analysis details suitable for use in the present invention may be found for instance in WO-A-2004/099763, which is incorporated by reference herein in its entirety.

Since the method of the invention is quick and straightforward, and relatively simple to perform, it may suitably be used for the automated detection of hospital outbreaks, i.e. when a significant (abnormally high) number of patients acquire infections within a short period of time, without there even being a prior suspicion of an outbreak and without requiring additional measurements or tests i.e. other than those already performed to determine the best course of treatment for the individual patient of which the isolate was obtained. An outbreak may be detected without prior suspicion of an outbreak and without requiring prior taxonomic classification of the micro-organism involved by classification of a micro-organism in a sample of interest using the instrument according to the invention. Then, determining the numbers of samples from different individuals with a specific infection over a certain period of time, whereby the finding of a larger-than-expected number of samples of a specific infection is indicative of an outbreak.

The method of the invention also allows for the tracing of a source of microbial infection or of contamination since it allows for the rapid determination of re-infection of a patient with the same strain. On the other hand, it can also prevent costly hygienic measures being taken if e.g. two methicillin-resistant *Staphylococcus aureus* (MRSA) infections are encountered on the same day, which are not caused by the same strain.

The method of the invention also allows for the monitoring of strain prevalence, since it gives information on earlier cases of infection with the same strain. An unusual prevalence of such infections points to a strain having colonized the hospital. This is detected automatically without requirement for further tests. At the same time it provides information regarding earlier cases of infection with the same strain and can send out an alert if such an infection was found within a certain (user-defined) prior time frame. No further separate/specific testing to establish such is needed. The method of the invention may also advantageously be used for monitoring changes in antibiograms at any geographical scale.

The person skilled in the art will understand that the method of the invention allows for the tracing of the source of contamination in many types of industry, particularly in the food industry, cosmetics industry and pharmaceutical industry. It is noted that the instrument and method of the invention may also be used in situations were micro-organisms are produced on purpose, e.g. in fermentation processes or in probiotic nutrition treatments using micro-organisms. In these situations, the micro-organism is very likely not eliminated, but on the contrary, the instrument is used to make sure that the micro-organism is present and stays present and adequate warnings should then be given to indicate that the organism has been lost or that spectral characteristics of the organism have changed.

By way of example, and not of limitation, Examples of the present invention will now be given.

EXAMPLE

Raman Spectroscopy

A schematic of the Raman spectroscopic measurement setup is shown in FIG. 1. Laser light of 785 nm from a diode laser 10 (Tiger Laser System 1000, Sacher LaserTechnik, Marburg, Germany) was guided into a Model 2500 High Performance Raman Module (Model 2500 HPRM) 30 (River Diagnostics B.V., Rotterdam, The Netherlands) by means of a single mode optical fiber 20. The Model 2500 HPRM emitted the laser light 40 through a pinhole 31 of 50 µm in diameter. The laser light was focused by a lens 50 with a numerical aperture of 0.7 in a dried microbial sample 80, deposited on a fused silica slide 70, on a translation stage 60 which could move the fused silica slide 70, in 2 directions perpendicular to the optical axis of lens 50. The laser power on the sample was about 150 mW. Lens 50 collected scattered light 90 from the sample, which followed the same optical path, as laser light 40 but in opposite direction back into the Model 2500 HPRM 30, through pinhole 31, which recorded the spectrum of the scattered light 90 in the wavenumber region between 340 and 2 450 cm$^{-1}$ by means of a charge-coupled device camera 100 optimized for operation in the red and the near-infrared spectral region (Model DU401-BR-DD-360. ANDOR, Belfast, UK) and coupled to a personal computer 110, where measured spectra were stored and processed.

Microbial Samples

Samples of five *Staphylococcus aureus* strains, obtained form the Department of Medical Microbiology of the Erasmus University Medical Center Rotterdam (Erasmus MC), The Netherlands (*S. aureus* 2398, *S. aureus* 3363, *S. aureus* 3534, *S. aureus* 4471, *S. aureus* 4942 (internal strain numbering of Erasmus MC)) and three *Pseudomonas aeruginosa* strains, obtained form the Department of Medical Microbiology of the Erasmus University Medical Center Rotterdam, The Netherlands (*P. aeruginosa* 28689, *P. aeruginosa* 28695, *P. aeruginosa* 27853 (internal strain numbering of Erasmus MC)) were streaked on Mueller Hinton agar plates (Merck, Darmstadt, Germany) and were cultured for 16 hours at 35° C. From these cultures, a calibrated 1 µl loop was filled with biomass from the third segment and suspended in 10 µl of distilled water. 4 µl of this suspension was transferred onto a fused silica substrate (Hellma Benelux, Rijswijk, The Netherlands) and allowed to dry in air at room temperature.

Samples of four *Mycobacterium* strains, obtained form the Rijksinstituut voor Volksgezondheid en Milieu (RIVM), Bilthoven, The Netherlands (*M. gordonae* 9900243, *M. xenopi* 9701961, *M.* spp 39-001SPA, *M.* spp 39-043SPA (internal strain numbering of RIVM)) were prepared by taking a loop of biomass from a *Mycobacterium* culture on Middlebrook 7H10-agar or Lowenstein-Jensen and suspending these in Mycobacteria Growth Indicator Tubes (MGIT; Becton Dickinson Microbiology Systems, Cockeysville, Md.). The tubes were incubated in a semi-automated incubation system (BACTEC™ MGIT™ 960 System, Becton Dickinson Microbiology Systems, Cockeysville, Md., USA). Tubes positive for microbial growth were indicated by the incubation system. To inactivate the Mycobacterium samples, positive cultures were centrifuged for 15 min at 3 660×g and the sediment was suspended in 1 ml normal saline and heated for 20 min at 80° C. Before Raman measurements were performed, the samples were washed three times with distilled water (1 wash: centrifugation for 1 minute at 12 000×g, removal of supernatant and suspension of sediment in 1 ml distilled water). The final sediment was suspended in 10 µl of distilled water of which 4 µL was transferred to a fused silica glass slide and allowed to dry in air at room temperature.

Measurement Protocol

Laser light 40 was focused at a location in the dried microbial sample 80 on the fused silica substrate 70. 500 consecutive Raman spectra were recorded at this location, each with a signal collection time of 1 second. This was repeated three times, each time at a different location in the dried microbial sample, for each of the five *S. aureus*-samples, two *P. aeruginosa* samples, and four *Mycobacterium*-samples.

Signal Analysis

Signal processing and analysis procedures were programmed in MATLAB version 7.1 (The Mathworks, Natick, Mass.).

Processing of Raman Spectra

For calibration of the wavenumber axis of the Raman spectra of microbial samples, the emission spectrum was measured of a Ne—Ar emission light source of which the positions of the spectral emission lines are precisely known, and which is incorporated in the Model 2500 HPRM, and the Raman spectrum was measured of a Raman calibration sample of inert material with precisely known Raman peaks, also incorporated in the Model 2500 HPRM. The emission lines of the Ne—Ar light source were used to convert pixel positions of the CCD camera 100 to absolute wavenumbers. The spectrum of the Raman calibration sample was used to determine the exact position of the laser emission line in absolute wavenumbers. The CCD camera pixel positions were then converted to relative wavenumbers by subtracting the laser line position (in absolute wavenumbers), from the pixel position (in absolute wavenumbers). The reproducibility of the calibration of pixel numbers in relative wavenumbers in the 400-1 800 cm$^{-1}$ spectral region was about 0.1 cm$^{-1}$. The wavelength dependent signal detection efficiency of the Raman measurement setup was corrected by measuring the fluorescence emission spectrum from a National Institute of Standards and Technology (NIST, Gaithersburg, Md., USA)-certified Standard Reference Material 2241 (SRM 2241—Relative Intensity Correction Standard for Raman Spectroscopy: 785 nm excitation), excited with laser light from laser 10. The recorded spectrum was divided by a calculated spectrum based on the NIST-provided fluorescence emission spectrum of the SRM 2241 sample, which would be recorded if the signal detection efficiency of the Raman instrument would be wavelength independent. This correction for the wavelength dependence of the signal detection efficiency of the measurement setup was reproducible to within 0.5%.

Background signal, generated in the optical components of the Raman measurement setup, including the signal of fused silica of 70 window, and due to dark current generated in the CCD camera, were separately recorded, and subtracted from the Raman spectra obtained from microbial samples 80.

Data Analysis

Determination of presence and spectral features of bleachable spectral components in Raman spectra of microbial samples All spectra obtained from microbial samples 80, were scaled by means of "standard normal variance" (SNV-)scaling applied to the 1 432-1 498 cm$^{-1}$ spectral region; i.e. the spectra were scaled such that for this region the mean signal intensity was set to zero and the signal intensity variance over this spectral region was set to one.

The presence of independent bleachable spectral components was determined by means of a Principal Components Analysis (Jolliffe, I. T., Principal component analysis. Springer series in statistics. 1986, New York: Springer Verlag) on each series of 500 spectra obtained from one location. The evolution of the scores of consecutively measured spectra on the first nine principal components was analyzed for each series of 500 spectra obtained from a location in a sample, in order to determine whether 1 or more independently bleaching components were present in the microbial samples.

In all cases only the first principal component contained significant spectral features above noise level, indicating the presence of a single bleachable component and in accordance with this only the scores on the first principal component showed a (significant) dependence on spectrum number.

For each series of 500 consecutive spectra obtained at a location in a sample, it was determined at which spectrum the intensity of the bleachable components had decreased by about 50%. All spectra from the start of a series of 500 spectra up to the 50%-spectrum were averaged. All spectra from the 50%-spectrum until the end of the series were also averaged. The difference spectrum of these averages was calculated to obtain a spectrum of the spectral components that had been bleached. For each sample the difference spectra obtained from the different series of 500 spectra were averaged to optimize the signal-to-noise ratio of the spectrum of the bleachable components. It will be obvious to the person skilled in the art that various other ways to determine the spectrum of the bleachable spectral components can be applied, including the use of multivariate spectra analysis methods, such as Principal Components Analysis, and making use of different choices of subdivision of the series of 500 spectra, e.g. subdivision in more than two sets of spectra, to arrive at a calculation of the bleachable component spectrum. For instance in case more than one bleachable component is present, characterized by the fact that different bleachable components bleach with different time-constant are present, such more elaborate methods may be used to obtain estimates of the spectra of the different bleachable components present in the samples.

For each sample the difference spectra obtained from the 3 series of 500 spectra were averaged to optimize the signal-to-noise ratio of the spectrum of the bleachable component.

Use of the Spectra of Bleachable Spectral Components to Reduce Signal Variance in Raman Spectra of Microbial Samples Extended Multiplicative Scatter Correction (EMSC) and Spectral Interference Subtraction (SIS)

Spectra were scaled using an EMSC approach with a 7$^{th}$ order polynomial background. Elimination of signal variance due to the bleachable spectral features in the bacterial spectra was performed by a technique called spectral interference subtraction (SIS), using the averaged difference spectra, obtained from bleaching different strains, as interferents. The two techniques were used in conjunction, in order to achieve a signal scaling that is not influenced by the presence of fluctuating fluorescence backgrounds or known interfering fluctuating signals like those of bleaching molecules.

Visualization of Effects of Method to Reduce Signal Variance Due to Bleachable Spectral Components: Hierarchical Clustering Analysis (HCA)

HCA was performed using one minus the squared correlation coefficient (1-R$^2$) between each pair of spectra in the analysis as distance measure. The correlation coefficient R between any two variables X and Y (X and Y having equal dimension) describes the tendency of the variables X and Y to change together, and is defined as:

$$R_{XY} = \frac{\sum (X - \overline{X})(Y - \overline{Y})}{\sqrt{\sum (X - \overline{X})^2} \sqrt{\sum (Y - \overline{Y})^2}}$$

Where X and Y are the variables, and $\overline{X}$ and $\overline{Y}$ are the average values of these variables. The squared correlation coefficient is thus the square of the above equation.

Ward's linkage algorithm was used to generate the hierarchical cluster tree; the dendrogram. Ward's linkage uses the incremental sum of squares as distance measure between two clusters r and s, i.e. the increase in the total within-cluster sum of squares as a result of joining clusters r and s. The within-cluster sum of squares of a cluster A (CSS$_A$) is defined as the sum of the squares of the distances between all N$_X$ objects in the cluster and the centroid X$_C$ of that cluster:

$$CSS_A = \sum_{i=1}^{N_A} (1 - R^2)^2_{X_i X_C},$$

where $$X_C = \frac{1}{N_X} \sum_{i=1}^{N_A} X_i$$

is the cluster center, and (1−R$^2$)$_{X_i X_C}$ is the distance between objects X$_i$ and X$_C$.

The increase d$_{css}$(r, s) in the total within-cluster sum of squares as a result of joining clusters r and s is the given by:

$$d_{css}(r,s) = CSS_{rs} - (CSS_r + CSS_s)$$

For two clusters r and s this distance can also be expressed as:

$$d(r, s) = N_r N_s \frac{(1 - R^2)^2_{rs}}{(N_r + N_s)}$$

where $(1-R^2)_{rs}$ is the distance between the cluster centers of clusters r and s, and $N_r$ and $N_s$ are the numbers of objects in clusters r and s respectively. Relations in the dendrogram are expressed as 'percentage dissimilarity' with d(r,s) as values.

Results

Figure 2:
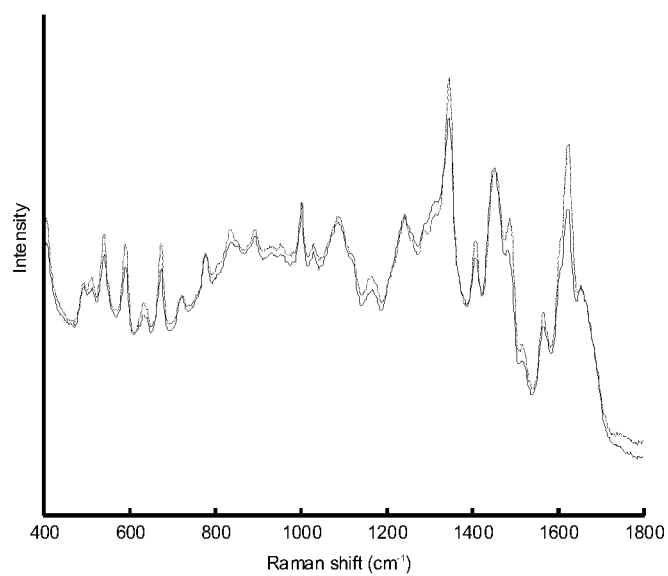
FIG. 2 shows the signal variance observed in Raman spectra of independent cultures of the same *P. aeruginosa* strain.

FIG. 2 shows an example of signal variance in certain regions of the Raman spectrum of a *P. aeruginosa* strain, as observed between Raman spectra obtained from samples based on independent cultures of this strain.

Figure 3:
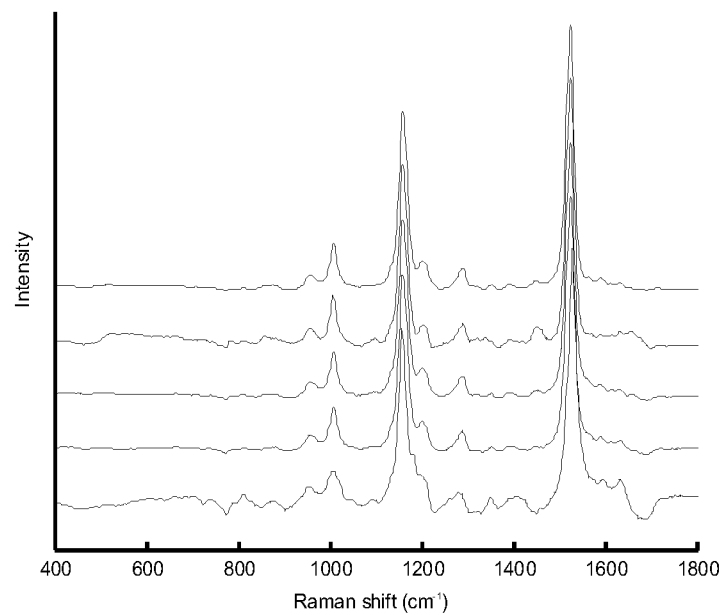
FIG. 3 shows the bleachable components of Raman spectra of *S. aureus* strains.

FIG. 3 shows the bleachable spectral components of the 5 strains of *S. aureus*. Although similar in appearance subtle differences between the bleachable component spectra obtained from the different *S. aureus* strains are observed, both in peak position of the intense band at about 1 520 cm$^{-1}$ as well as in fine structure of less intense spectral features.

Figure 4:
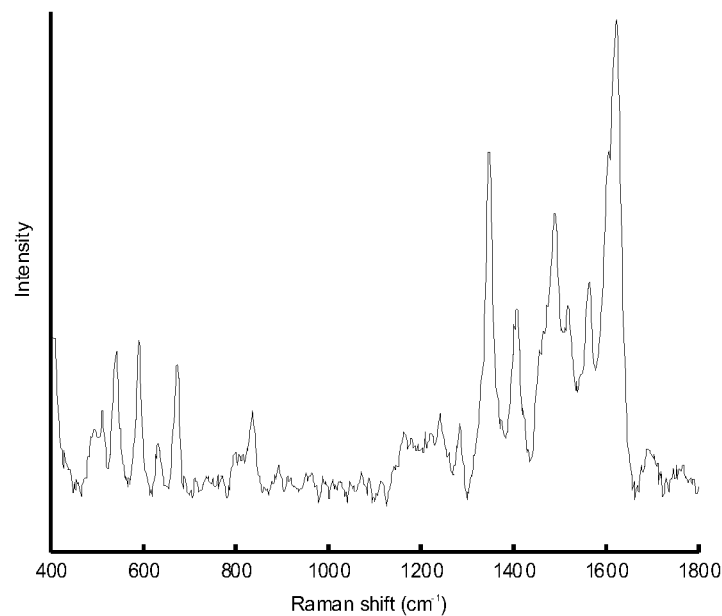
FIG. 4 shows bleachable components of Raman spectra of *P. aeruginosa* strains.

FIG. 4 shows the bleachable components of 3 strains of *P. aeruginosa*. The bleachable components spectra determined for these 3 strains were identical.

Figure 5:
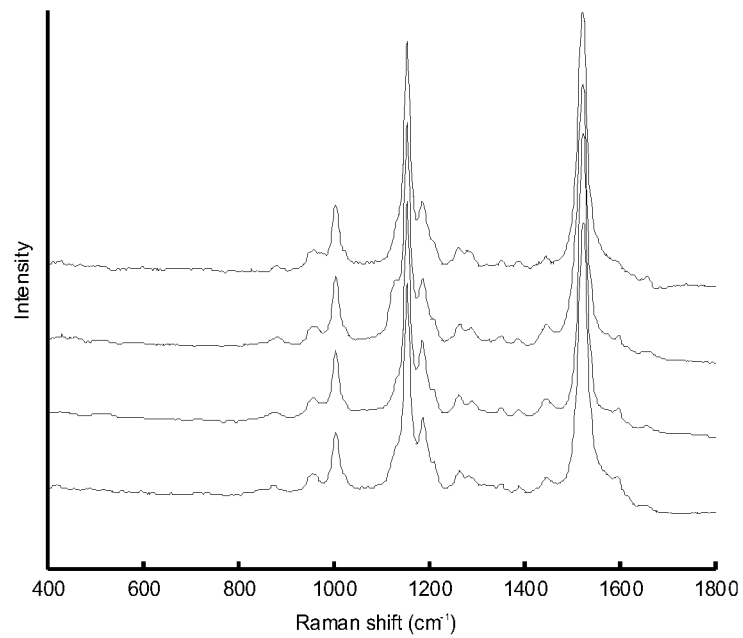
FIG. 5 shows bleachable components of Raman spectra of 4 *Myobacterium* strains.

FIG. 5 shows the bleachable spectral components of the 4 *Mycobacterium* strains. The main features resemble the bleachable components spectra of the *S. aureus* strains. Differences with the bleachable component spectra of *S. aureus* are apparent e.g. in the 1 200-1 500 cm$^{-1}$ spectral interval.

Effect of Method on Classification of *S. Aureus* Strains

Figure 6A:
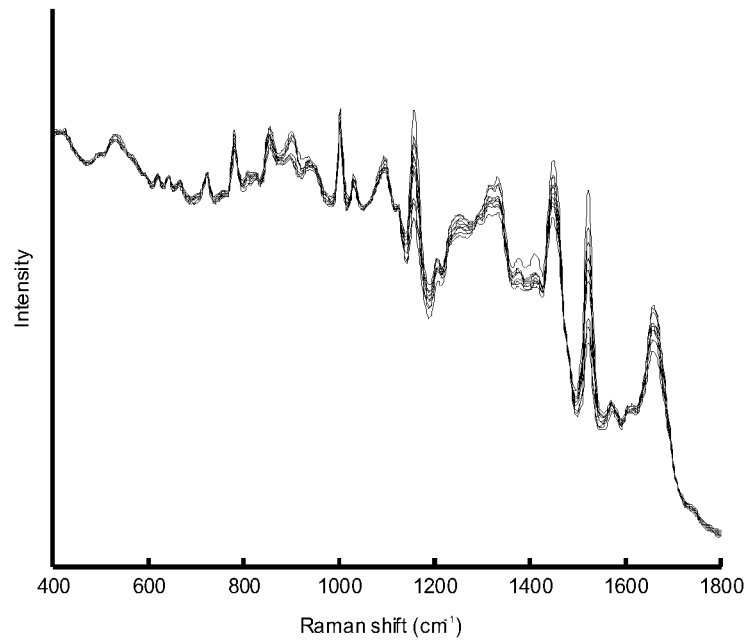
FIG. 6A shows Raman spectra of 5 MRSA-strains without correction for signal variance due to bleachable spectral components.
Figure 6B:
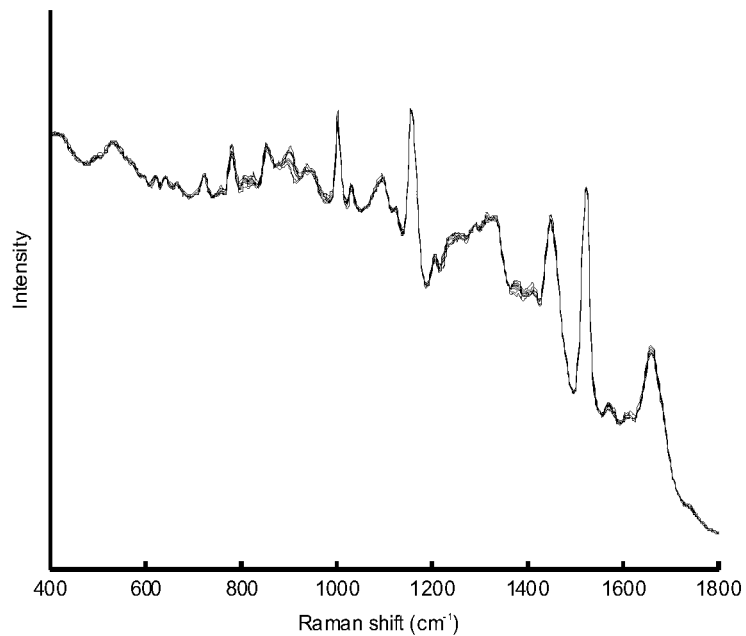
FIG. 6B shows Raman spectra of 5 MRSA-strains after correction for signal variance due to bleachable spectral components.
Figure 6C:
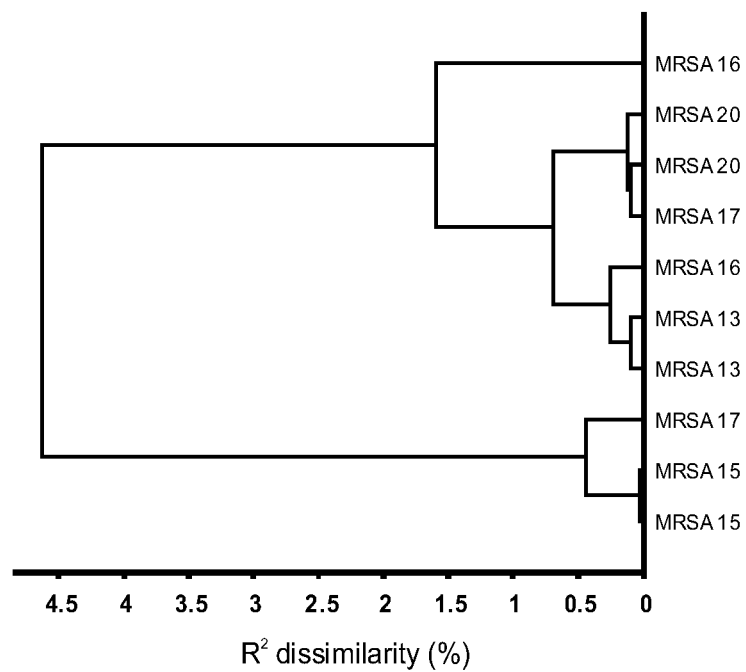
FIG. 6C shows a dendrogram based on Hierarchical clustering analysis of the set of Raman spectra of 5 MRSA strains of FIG. 6A.
Figure 6D:
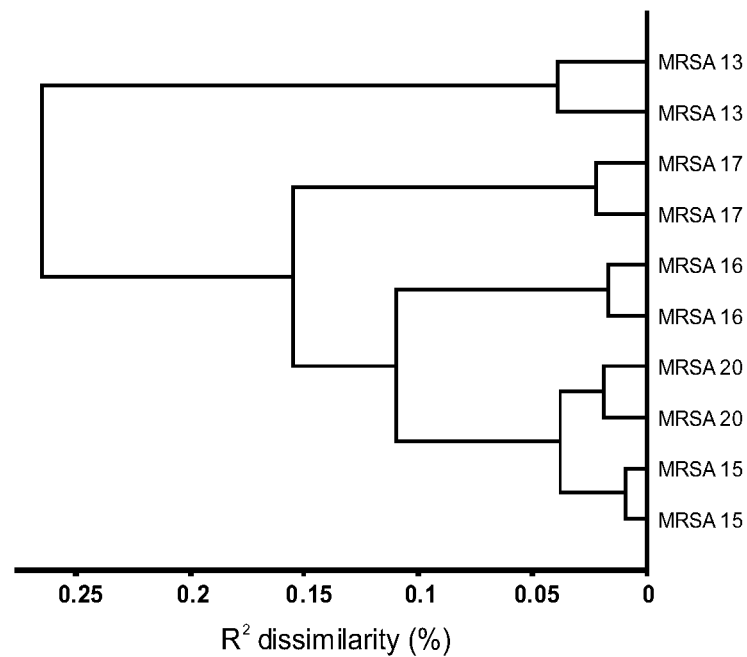
FIG. 6D shows a dendrogram based on Hierarchical clustering analysis of the set of Raman spectra of 5 MRSA strains of FIG. 6B.

Samples were prepared of 5 genetically unrelated methicillin resistant *S. aureus* (MRSA) strains, in the same way as described for *S. aureus* 2398, *S. aureus* 3363, *S. aureus* 3534, *S. aureus* 4471, *S. aureus* 4942. MRSA strains nr. 13, 15, 16, 17 and 20, were taken from the well-characterized strain collection that was used previously by Van Belkum et al. (van Belkum, A. et al., Assessment of resolution and intercenter reproducibility of results of genotyping *Staphylococcus aureus* by pulsed-field gel electrophoresis of SmaI macrorestriction fragments: a multicenter study. J Clin Microbiol, 1998. 36(6): p. 1653-1659.) From each sample on the optical substrate 50 spectra were collected at random locations, each with a sample collection time of 1 second. Spectra were calibrated and pre-processed as described above. Outlier spectra, defined as having a correlation coefficient lower than 99.6% to the median spectrum of a set obtained from one sample, were removed. The remaining spectra were averaged per sample. This experiment was repeated on a separate day to yield 2 independent replicates per strain. FIG. 6A shows spectra before correction of the signal variance due to bleachable spectral components and FIG. 6B shows the same spectra after correction. FIGS. 6C and 6D show dendrograms based on hierarchical clustering analysis for the uncorrected and corrected spectra respectively. It is obvious that the collection of uncorrected spectra shows greater signal variance (FIG. 6A) than the collection of corrected spectra (FIG. 6B). The corresponding dendrograms (FIGS. 6C and 6D) show the greater degree of dissimilarity between uncorrected spectra than between corrected spectra. Also, in the dendrogram based on uncorrected spectra, clustering of spectra, obtained from 2 independently prepared sets of samples of the 5 strains, does not always take place on the basis of strain-type. In the dendrogram based on corrected spectra (FIG. 6D), clustering does take place on the basis of strain-membership, indicating that intra-strain signal variance was reduced to a level below that of inter-strain signal variance.

Effect of Method on Classification of *P. Aeruginosa* Strains

Figure 7A:
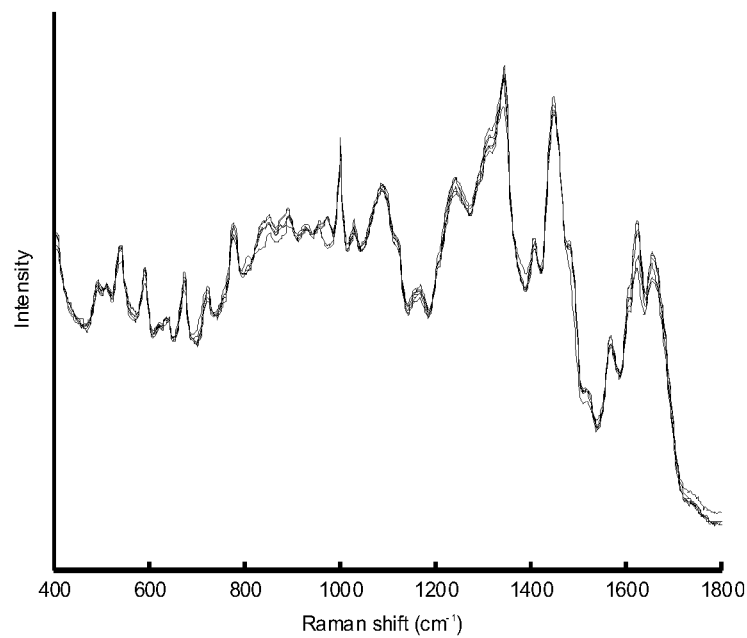
FIG. 7A shows Raman spectra of 3 *P. aeruginosa* strains without correction for signal variance due to bleachable spectral components.
Figure 7B:
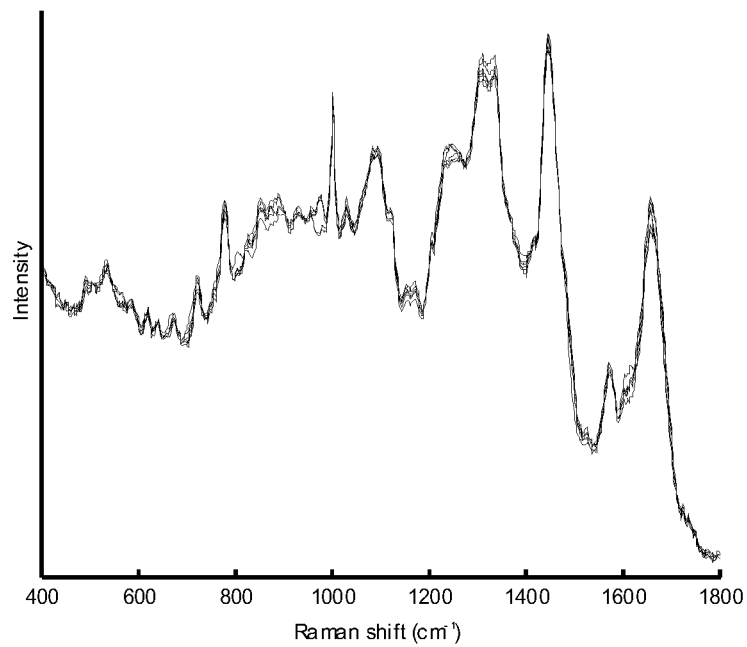
FIG. 7B shows Raman spectra of 3 *P. aeruginosa* strains after correction for signal variance due to bleachable spectral components.
Figure 7C:
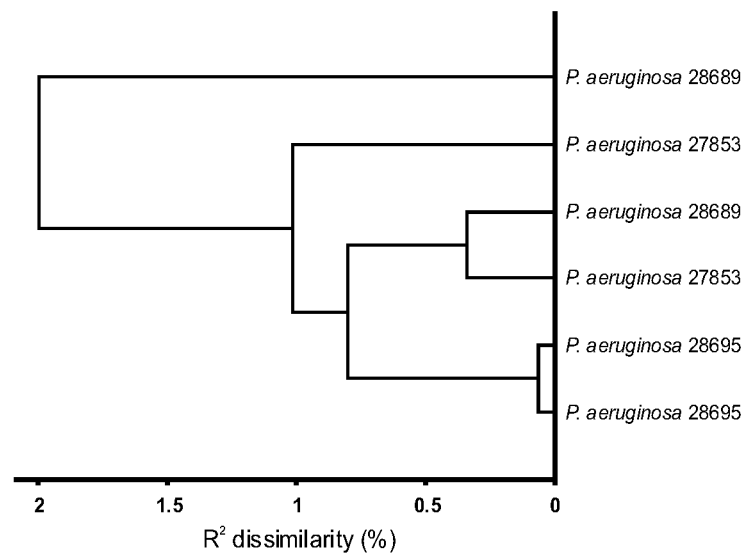
FIG. 7C shows a dendrogram based on Hierarchical clustering analysis of the set of spectra of 3 *P. aeruginosa* strains of FIG. 7A.
Figure 7D:
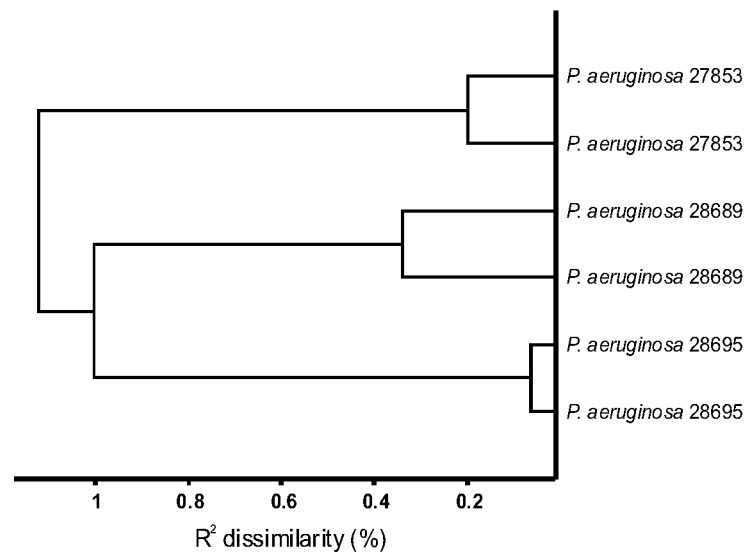
FIG. 7D shows a dendrogram based on Hierarchical clustering analysis of the set of spectra of 3 *P. aeruginosa* strains of FIG. 7B.

Samples were prepared of the *P. aeruginosa*-strains (*P. aeruginosa* 28689, *P. aeruginosa* 28695, *P. aeruginosa* 27853), which were used to determine the bleachable spectral components. From each microbial sample 80, on the optical substrate 70, 50 spectra were collected at random locations, each with a sample collection time of 1 second. Spectra were processed as described earlier. Outlier spectra, defined as having a correlation coefficient lower than 99.6% to the median spectrum of a set obtained from one sample, were removed. The remaining spectra were averaged per sample. This experiment was repeated on a separate day to yield 2 independent replicates per strain. FIG. 7A shows spectra before correction of the signal variance due to bleachable spectral components and FIG. 7B shows the same spectra after correction. FIGS. 7C and 7D show dendrograms based on hierarchical clustering analysis for the uncorrected and corrected spectra respectively. The collection of uncorrected spectra shows greater signal variance (FIG. 7A) than the collection of corrected spectra (FIG. 7B). The corresponding dendrograms (FIGS. 7C and 7D) show a greater degree of dissimilarity between uncorrected spectra than between corrected spectra. Also, in the dendrogram based on uncorrected spectra (FIG. 7C), clustering of spectra, obtained from 2 independently prepared sets of samples of the 3 strains, does not always take place on the basis of strain-type. In the dendrogram based on corrected spectra (FIG. 7D), clustering does take place on the basis of strain-membership, indicating that intra-strain signal variance was reduced to a level below that of inter-strain signal variance.

Effect of Method on Classification of *Mycobacterium*-Strains

Samples were prepared of 5 *Mycobacterium* strains (RIVM identification numbers: 015SP2N, 157SPA, 121SP2A, 161SP2N, 163SP2N). From each microbial sample 80 on the optical substrate 70, 50 spectra were collected at random locations, each with a sample collection time of 1 second. Spectra were processed as described earlier. Outlier spectra, defined as having a correlation coefficient lower than 99.6% to the median spectrum of a set obtained from one sample, were removed. The remaining spectra were averaged per sample. This experiment was repeated on a separate day to yield 2 independent replicates per strain.

Figure 8A:
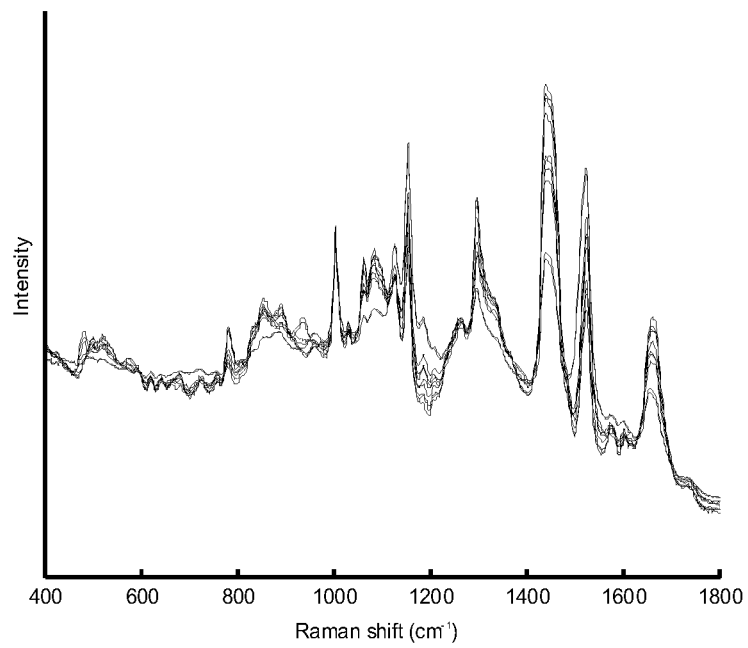
FIG. 8A shows Raman spectra of 5 *Myobacterium* strains, without correction for signal variance due to bleachable spectral components.
Figure 8B:
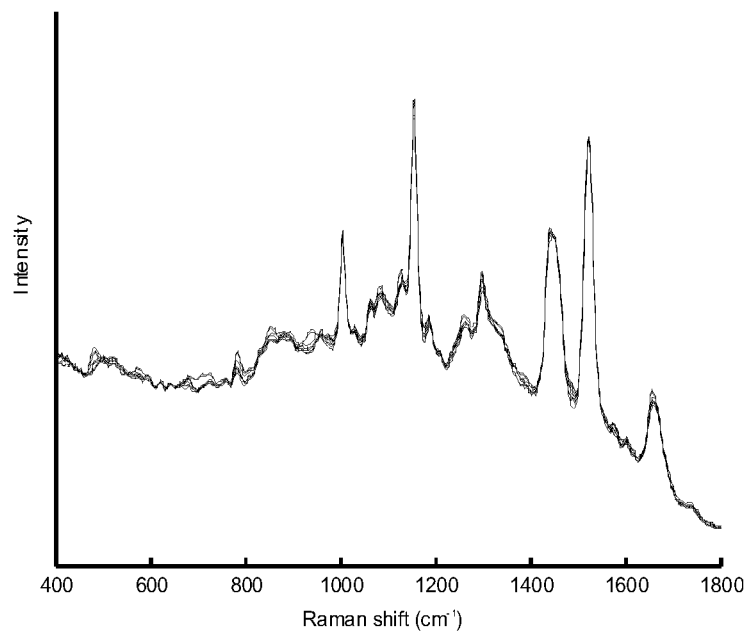
FIG. 8B shows Raman spectra of 5 *Myobacterium* strains after correction for signal variance due to bleachable spectral components.
Figure 8C:
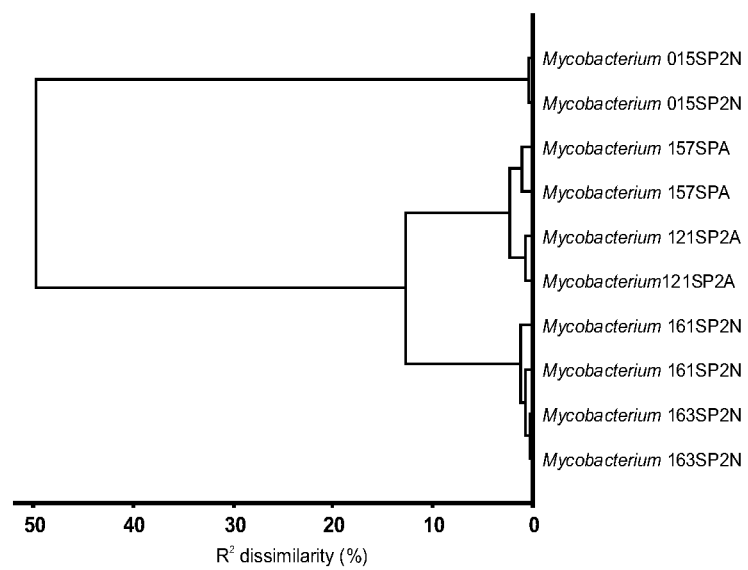
FIG. 8C shows a dendrogram based on Hierarchical clustering analysis of the set of spectra of 5 *Myobacterium* strains of FIG. 8A.
Figure 8D:
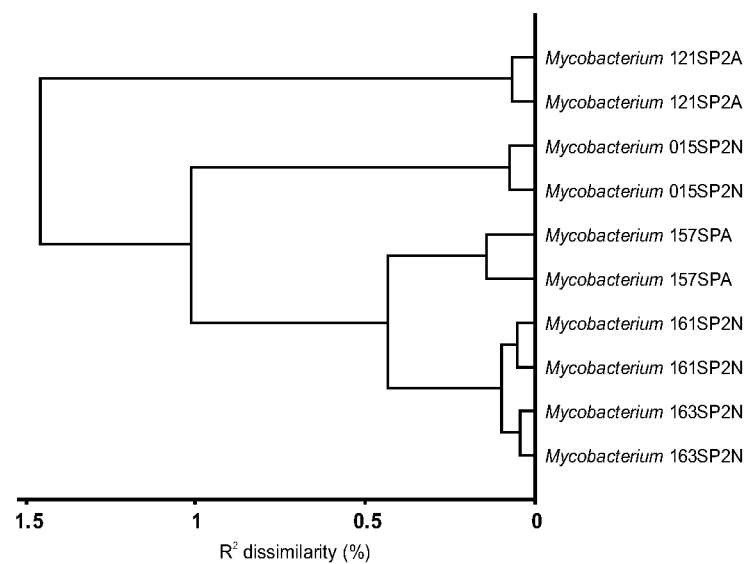
FIG. 8D shows a dendrogram based on Hierarchical clustering analysis of the set of spectra of 5 *Myobacterium* strains of FIG. 8B.

FIG. 8A shows spectra before correction of the signal variance due to bleachable spectral components and FIG. 8B shows the same spectra after correction. FIGS. 8C and 8D show dendrograms based on hierarchical clustering analysis for the uncorrected and corrected spectra respectively. The collection of uncorrected spectra shows greater signal variance (FIG. 8A) than the collection of corrected spectra (FIG. 8B). The corresponding dendrograms (FIGS. 8C and 8D) show a greater degree of dissimilarity between uncorrected spectra than between corrected spectra. Also, in the dendrogram based on uncorrected spectra (FIG. 8C), clustering of spectra, obtained from 2 independently prepared sets of samples of the 5 strains, does not always take place on the basis of strain-type (strains 161SP2N and 163SP2N). In the dendrogram based on corrected spectra (FIG. 8D), clustering does take place on the basis of strain-membership, indicating that intra-strain signal variance was reduced to a level below that of inter-strain signal variance.

The invention claimed is:

1. A method for typing of a strain of a microorganism belonging to a microbial species, using vibrational spectroscopy, comprising:

Measuring a spectrum of a microorganism strain belonging to said species in a test sample;

Prior to said measuring, identifying one or more vibrational spectroscopic signal contributions of bleachable components present in one or more microorganism strains of said species by:

Subjecting each of said one or more strains belonging to said species to a photobleaching process;

Recording for each of said one or more strains belonging to said species at least two vibrational spectra at different stages of the photobleaching process; and Determining for each of said one or more strains belonging to said species the signal contributions of bleachable components by analysis of said spectra obtained at different stages of the photobleaching process;

Calculating a corrected spectrum of said microorganism strain in said test sample by substantially eliminating said signal contributions due to bleachable components identified in said determining step from said measured spectrum; and Typing said microorganism strain sample by determining the similarity of said corrected spectrum to a dataset of corrected spectra of microorganism strain samples belonging to said species, wherein signal contributions due to bleachable components have been substantially eliminated from the spectra of said dataset.

2. The method according to claim 1, wherein said photobleaching of said sample is performed under laser light.

3. The method according to claim 2, wherein said photobleaching is performed for at least 1 second.

4. The method according to claim 2, wherein said photobleaching is performed using the same laser light source as is used for measuring said spectrum of said microorganism strain in said test sample.

5. The method according to claim 1, wherein obtaining said reference data set further comprises:

Obtaining multiple vibrational spectra recorded over a period of time from said one or more strains of said species containing bleachable components, while said one or more strains of said species are being subjected to photo-bleaching, wherein the one or more vibrational spectroscopic signal contributions of said bleachable components are identified from multiple spectra thus obtained.

6. The method according to claim 5, wherein said multiple vibrational spectra comprise spectra recorded from spatially separated locations of said one or more strains of said species.

7. The method according to claim 6, wherein said one or more strains of said species is a culture of micro-organisms.

8. The method according to claim 6, wherein said one or more strains of said species is a pure culture.

9. The method according to claim 1, further comprising:
Using Extended Multiple Scatter Correction—Spectral Interference Subtraction (EMSC SIS) for said calculating of said corrected spectrum.

10. The method according to claim 1, wherein said reference data set consists of spectra obtained from substantially non-photo-bleached micro-organisms.

11. The method according to claim 1, wherein said reference data set consists of spectra obtained from substantially non-photo-bleached micro-organisms and of spectra obtained from substantially photo-bleached micro-organisms.

12. The method according to claim 1, wherein typing said microorganism strain comprises hierarchically clustering the vibrational spectroscopic information of said corrected spectrum of said microorganism strain in said test sample for typing and identification purposes.

13. The method according to claim 1, wherein typing said microorganism strain comprises:

Performing principal component analysis of said corrected spectrum of said microorganism strain in said test sample to obtain Principal Component scores; and hierarchically clustering the principal component scores for typing and identification purposes.

14. The method according to claim 1 wherein said microorganism belonging to a microbial species is a strain belonging to a species selected from *Staphylococcus aureus*, *Pseudomonas aeruginosa*, and *Mycobacterium*.

15. The method according to claim 1 wherein the vibrational spectroscopy is at a wavelength of at least 630 nm.

16. The method according to claim 1 wherein the vibrational spectroscopy is at a wavelength of 785 nm.

17. The method according to claim 1 wherein the vibrational spectroscopy is at a wavelength of 830 nm.

* * * * *

UNITED STATES PATENT AND TRADEMARK OFFICE
CERTIFICATE OF CORRECTION

| | | |
|---|---|---|
| PATENT NO. | : 9,194,803 B2 | Page 1 of 1 |
| APPLICATION NO. | : 12/669366 | |
| DATED | : November 24, 2015 | |
| INVENTOR(S) | : Maquelin et al. | |

It is certified that error appears in the above-identified patent and that said Letters Patent is hereby corrected as shown below:

In the claims:

Claim 5, line 1, delete "obtaining" to and ending "set" in claim 5, line 2 and insert --said determining signal contributions of bleachable components--

Signed and Sealed this
Tenth Day of May, 2016

Michelle K. Lee
*Director of the United States Patent and Trademark Office*